(12) United States Patent
Lyons et al.

(10) Patent No.: US 8,241,320 B2
(45) Date of Patent: Aug. 14, 2012

(54) SURGICAL INSTRUMENT

(75) Inventors: Edwin Lyons, Galway (IE); Douglas J. Rose-Innes, Gwent (GB); Robert J. Brewer, Newport (GB)

(73) Assignee: Gyrus Medical Limited, Cardiff (GB)

( * ) Notice: Subject to any disclaimer, the term of this patent is extended or adjusted under 35 U.S.C. 154(b) by 764 days.

(21) Appl. No.: 12/320,017

(22) Filed: Jan. 14, 2009

(65) Prior Publication Data
US 2009/0187185 A1 Jul. 23, 2009

Related U.S. Application Data

(60) Provisional application No. 61/006,715, filed on Jan. 29, 2008.

(30) Foreign Application Priority Data

Jan. 18, 2008 (GB) .................................. 0800968.0

(51) Int. Cl.
*A61B 17/00* (2006.01)
*A61B 18/18* (2006.01)
(52) U.S. Cl. .......................................... 606/205; 606/51
(58) Field of Classification Search .............. 606/41, 606/130, 51, 52, 205–207; 604/95.04
See application file for complete search history.

(56) References Cited

U.S. PATENT DOCUMENTS

| | | | |
|---|---|---|---|
| 5,251,638 A | 10/1993 | Cottone, Jr. et al. | |
| 5,868,785 A * | 2/1999 | Tal et al. | 606/207 |
| 2004/0158233 A1 | 8/2004 | DiCesare et al. | |
| 2006/0190034 A1 * | 8/2006 | Nishizawa et al. | 606/205 |
| 2007/0055228 A1 * | 3/2007 | Berg et al. | 606/41 |

FOREIGN PATENT DOCUMENTS

| | | |
|---|---|---|
| DE | 20302791 U1 | 5/2003 |
| EP | 1258224 A1 | 11/2002 |
| WO | 02/32324 A2 | 4/2002 |

OTHER PUBLICATIONS

Search Report issued in corresponding Application No. GB 0800968.0, (Date of Search: Jun. 10, 2008).

* cited by examiner

*Primary Examiner* — Jackie Ho
*Assistant Examiner* — Weng Lee
(74) *Attorney, Agent, or Firm* — Nixon & Vanderhye, PC

(57) ABSTRACT

An articulated surgical instrument includes a handle, an actuating assembly associated with the handle, and a shaft including a proximal end coupled to the handle, a deflectable portion and an end effector. Distal portions of deflection wires are connected to the shaft. Proximal portions of the wires are connected to the actuating assembly. Movement of the actuating assembly moves the deflection wires to cause a deflection of the deflectable portion. The actuating assembly includes one or more actuators and one or more slider members associated with the actuators and connected to the deflection wires. The slider members are movable linearly between first and second positions, the proximal portions of the deflection wires being connected to the slider members. One of the actuators and slider members has a cam track and the other has a cam follower, such that movement of an actuator by the user of the instrument causes a linear movement of a slider member from its first position to its second position, so as to move the deflection wires causing a corresponding deflection of the deflectable portion.

15 Claims, 5 Drawing Sheets

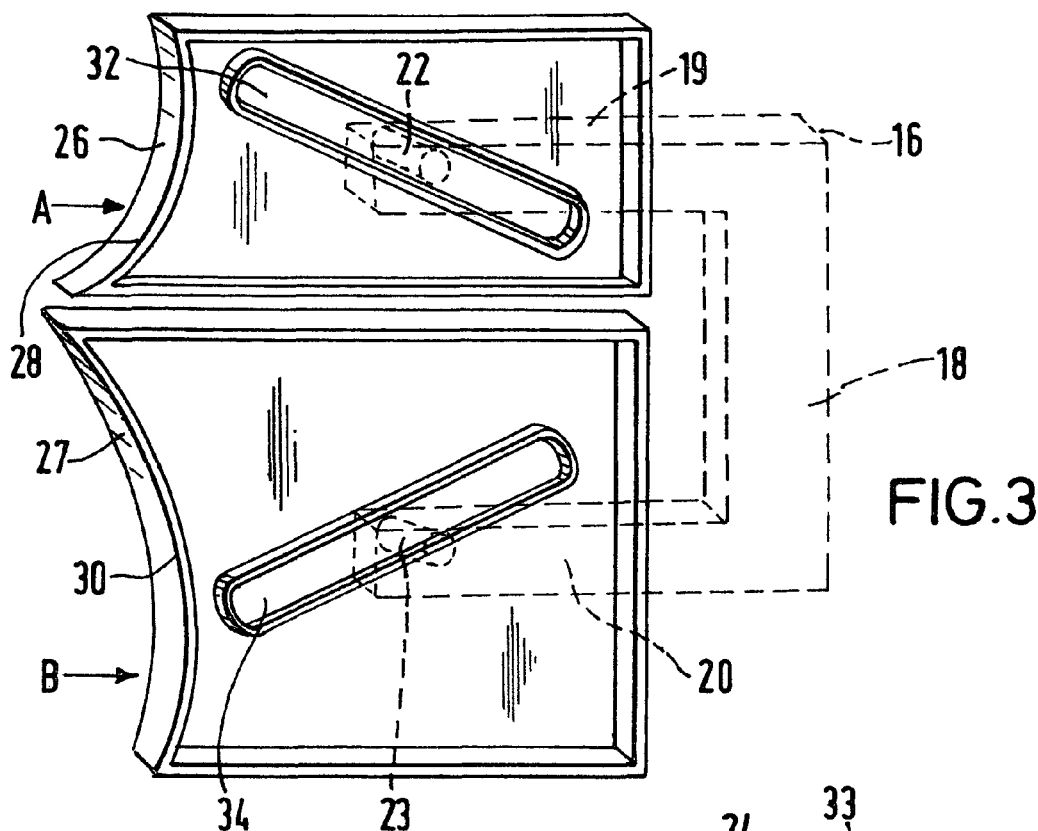
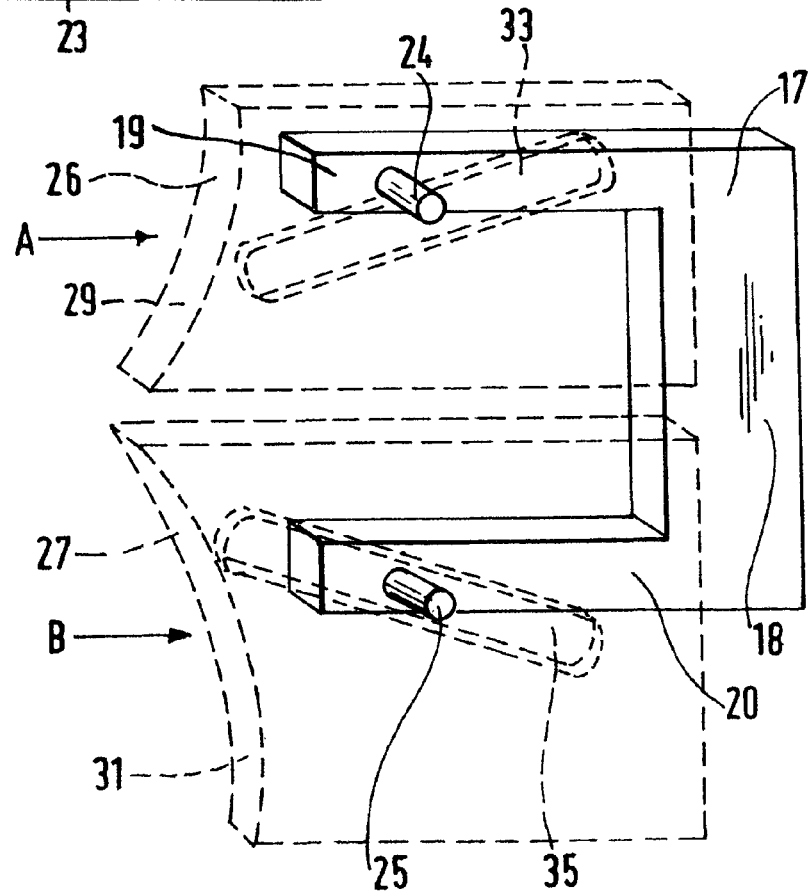

SURGICAL INSTRUMENT

CROSS-REFERENCE TO RELATED APPLICATION

This application claims the benefit of Provisional Application No. 61/006,715, filed Jan. 29, 2008, the entire contents of which are hereby incorporated by reference in this application.

FIELD OF INVENTION

This invention relates to an articulated surgical instrument such as a forceps, or to an electrosurgical instrument for use in the treatment of tissue.

BACKGROUND OF INVENTION

U.S. Pat. No. 6,283,960 discloses an articulated surgical instrument in which the distal end of the shaft of the instrument is articulated by the arcuate movement of a scissors-type handle. The present invention attempts to provide an improvement to this type of articulation mechanism.

SUMMARY OF INVENTION

The present invention provides an articulated surgical instrument comprising:
a handle;
an actuating assembly associated with the handle;
a shaft including a proximal end, a deflectable portion and an end effector, the proximal end of the shaft being coupled to the handle; and
at least one deflection wire, the or each deflection wire having a proximal portion and a distal portion, the or each distal portion being connected to the shaft, and the or each proximal portion being connected to the actuating assembly, movement of the actuating assembly moving the or each deflection wire to cause a deflection of the deflectable portion,
wherein the actuating assembly comprises at least one actuator and a respective slider member associated with the or each actuator, the or each slider member being movable linearly between a first position and a second position, the proximal portion of the or each deflection wire being connected to the associated slider member, a first one of the or each actuator and associated slider member having a cam track and the other having a cam follower, such that movement of the or each actuator by the user of the instrument causes a linear movement of the associated slider member from its first position to its second position so as to move at least one of the deflection wires causing a corresponding deflection of the deflectable portion.

Preferably, the or each least one actuator is a button movable linearly between a first position and a second position. By ensuring that both the slider member and the button move linearly, a minute deflection of the flexible portion of the instrument can be carefully controlled by the user of the instrument, more accurately than if arcuate movement of one of the components about a pivot is required. Conveniently, the linear movement of the or each button is in a direction orthogonal to the linear movement of the or each slider member.

In a preferred embodiment, there is provided at least first and second deflection wires and respective first and second slider members. In this way, one deflection wire acts to deflect the deflectable portion, and the other wire acts to return the deflectable portion to its initial position after deflection. If a second deflection wire is not provided, it may be necessary to provide some other return mechanism, such as a spring biasing mechanism for the deflectable portion. The term "deflection wire" is meant to include any structure capable of transmitting movement of the actuating mechanism to perform the deflection of the shaft. In addition to a wire, the term could conceivably include a cable formed of a plurality of wires twisted together, or even a more solid structure such as a push rod.

Preferably, the first deflection wire is connected to the first slider member, and the second deflection wire is connected to the second slider member. In one convenient arrangement, the first and second slider members are each constituted by respective halves of a single slider assembly, each half being linearly movable with respect to the other. Preferably, a first actuator constitutes said at least one actuator, the first actuator being provided with first and second cam tracks, and the first and second slider members each have a cam follower, the cam follower of the first slider member being received in the first cam track, and the cam follower of the second slider member being received in the second cam track.

The first and second cam tracks are preferably oriented in different directions, such that the movement of the first actuator causes the first slider member to move in a first direction and the second slider member to move in a different direction. Preferably, the movement of the first actuator causes the second slider member to move in an opposite direction to that of the first slider member. In this way, the first slider member moves the first deflection wire to deflect the surgical instrument. At the same time, the second slider member moves in the opposite direction to move the second deflection wire to provide sufficient slack for the deflection to take place. When the first actuator is released, the slider members return to their original positions, with the second deflection wire pulling the deflectable portion back into its original configuration.

In this arrangement, the instrument may further comprise a second actuator for actuating a locking mechanism adapted to lock the deflection wires in position.

In an alternative arrangement, there is provided first and second actuators. Preferably, the first and second actuators each are provided with first and second cam tracks, and the first and second slider members each have two cam followers, the cam followers of the first slider member being received in the first and second cam tracks of the first actuator, and the cam followers of the second slider member being received in the first and second cam tracks of the second actuator. In this way, the surgical instrument is capable of two-way deflection, the first actuator initiating deflection in a first direction, and the second actuator initiating deflection in a second direction.

Conveniently, the first and second cam tracks of each actuator are oriented in different directions, such that the movement of the first actuator causes the first slider member to move in a first direction and the second slider member to move in the opposite direction, and the movement of the second actuator causes the second slider member to move in the first direction and the first slider member to move in the opposite direction. Typically, the movement of the first actuator causes a corresponding opposite movement of the second actuator, and the movement of the second actuator causes a corresponding opposite movement of the first actuator. As described above, the depression of the second actuator will, therefore, cause deflection of the instrument in the opposite direction to that caused by the depression of the first actuator.

Conceivably, the surgical instrument is a forceps instrument, in which case the end effector is a pair of jaws. Alternatively, the instrument is an electrosurgical instrument, in which case the end effector includes an electrosurgical electrode. Conceivably, the electrosurgical instrument is bipolar, and the end effector is a bipolar electrode assembly.

BRIEF DESCRIPTION OF THE DRAWINGS

The invention will now be described in more detail, by way of example only, with reference to the drawings, in which;

FIGS. 3 and 4 are sectional close-up views of parts of the actuating mechanism of the instrument of FIG. 1;

DETAILED DESCRIPTION OF THE INVENTION

Figure 1:
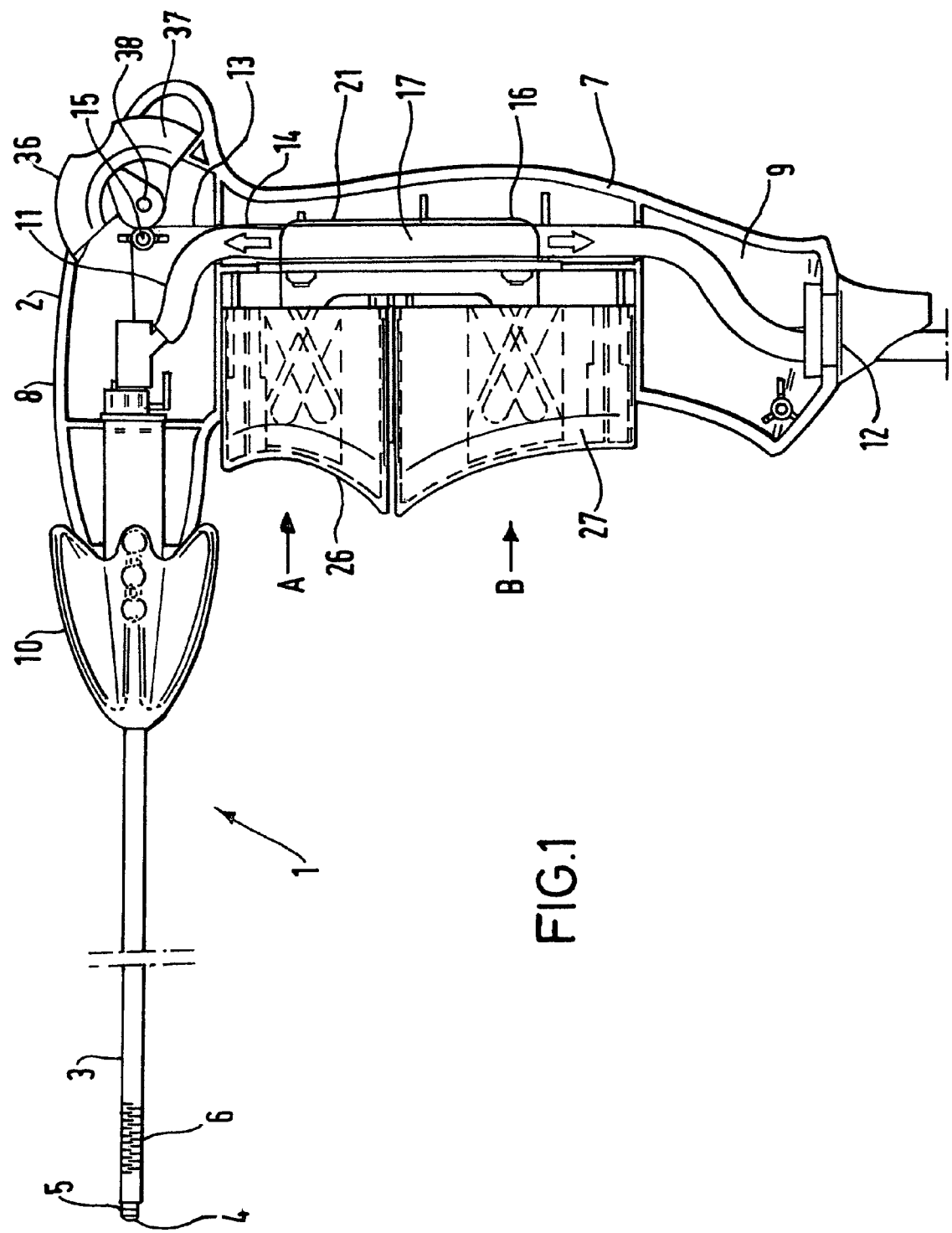
FIG. 1 is a schematic sectional view of a surgical instrument constructed in accordance with the invention.
Figure 2:
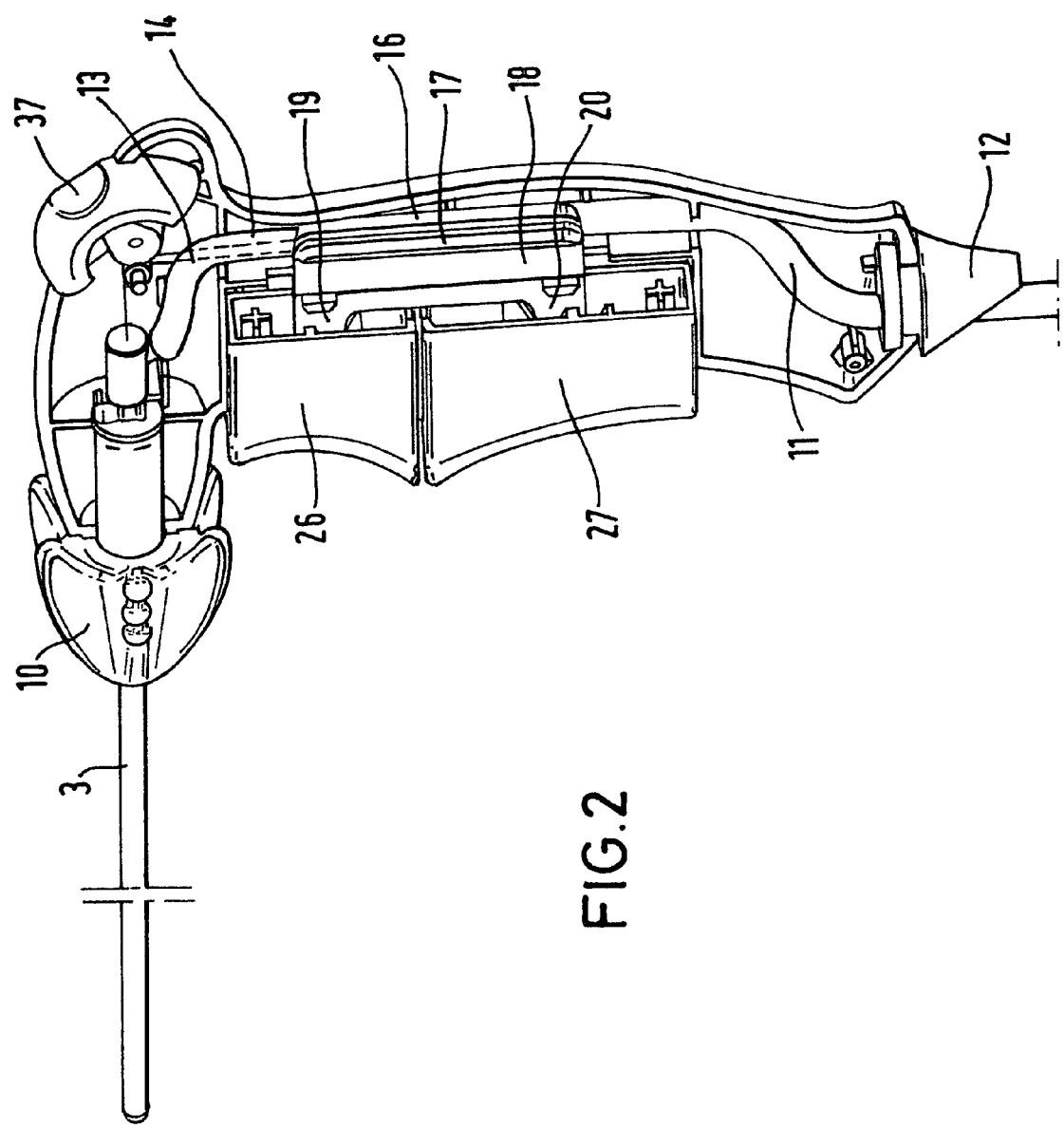
FIG. 2 is a rear perspective view, partly in section, of the instrument of FIG. 1.

Referring to FIGS. 1 to 5, an articulated surgical instrument is shown generally at 1, and comprises a handle 2, a shaft 3 and an end effector 4. The end effector 4 comprises a bipolar electrosurgical assembly 5, the construction of which is common in the field and is exemplified by the disclosure of U.S. Pat. No. 6,004,319. The shaft 3 includes a deflectable portion 6, the construction of which is again common in the field, and exemplified by U.S. Pat. No. 6,749,560. The disclosures of these two patent specifications are herein incorporated by way of reference.

The handle 2 comprises a housing 7 comprising an upper part 8 and a lower part 9. The shaft 3 is connected to the upper part 8 of the housing 7 by way of a swivel mechanism 10, the rotation of which causes a corresponding rotation of the shaft, and hence of the end effector 4. The shaft 3 has a hollow lumen, which provides a suction passage, and is connected to a suction tube 11, which traverses the handle 2 and exits the lower part 9 of the housing 7 via a strain relief element 12. The lumen also contains two deflection cables 13 and 14, which are used to deflect the portion 6. The cables 13 and 14 exit the shaft 3, pass over a pulley 15 and are connected to two slider members 16 and 17 contained within the housing 7. The deflection cable 13 is connected to the slider member 16, while the deflection cable 14 is connected to the slider member 17. The slider members 16 and 17 will be described in more detail in the following paragraphs.

Each slider member 16, 17 comprises a body portion 18, and first and second legs 19 and 20. Each body portion 18 includes an attachment feature 21, for the connection of a respective one of the deflection cables 13 and 14. The legs 19 and 20 of the slider member 16 contain pegs 22 and 23, which act as cam followers in a cam mechanism to be described. In a similar fashion, the legs 19 and 20 of the slider member 17 contain pegs 24 and 25. The slider members 16 and 17 are disposed in a corresponding back-to-back arrangement, with the pegs 22 and 23 extending on one side of the slider members, and the pegs 24 and 25 extending on the opposite side of the slider members. The slider members 16 and 17 are disposed for sliding movement within the lower part 9 of the housing 7.

The slider members 16 and 17 are actuated by first and second buttons 26 and 27. Each of the buttons 26 and 27 is formed by first and second moulded half-shells, the button 26 being formed by half-shells 28 and 29, and the button 27 by half-shells 30 and 31. Referring to the first button 26, the half-shell 28 includes a cam track in the form of a slot 32 in which the peg 22 of the slider member 16 is constrained. The slot 32 is disposed diagonally with respect to the direction of movement "A" of the button 26, running from upper to lower in the direction of movement of that button. Conversely, the opposite half-shell 29 of the button 26 is provided with a slot 33, in which the peg 24 of the slider member 17 is constrained. The slot 33 is also disposed diagonally with respect to the direction of movement "A" of the button 26, this time running from lower to upper with respect to the direction of movement of that button. Thus, when the button 26 is depressed, the slot 32 acts on the peg 22 to cause the slider member 16 to move upwardly within the lower part 9 of the housing 7. Conversely, the slot 33 acts on the peg 24 to cause the slider member 17 to move downwardly within the lower part 9 of the housing 7.

The second button 27 is constructed in a similar fashion. The half-shell 30 has a slot 34 in which the peg 23 of the slider member 16 is constrained. This slot 34 runs diagonally from lower to upper with respect to the direction of movement "B" of the button 27. The half-shell 31 has a slot 35 in which the peg 25 of the slider member 17 is constrained. The slot 35 runs diagonally from upper to lower with respect to the direction of movement "B" of the button 27. Thus, when the button 26 is depressed, and the slider member 16 moves upwardly and the slider member 17 moves downwardly, the cam action of the pegs 23 and 25 in the slots 34 and 35 causes the button 27 to move outwardly as shown in FIG. 5.

Figure 5:
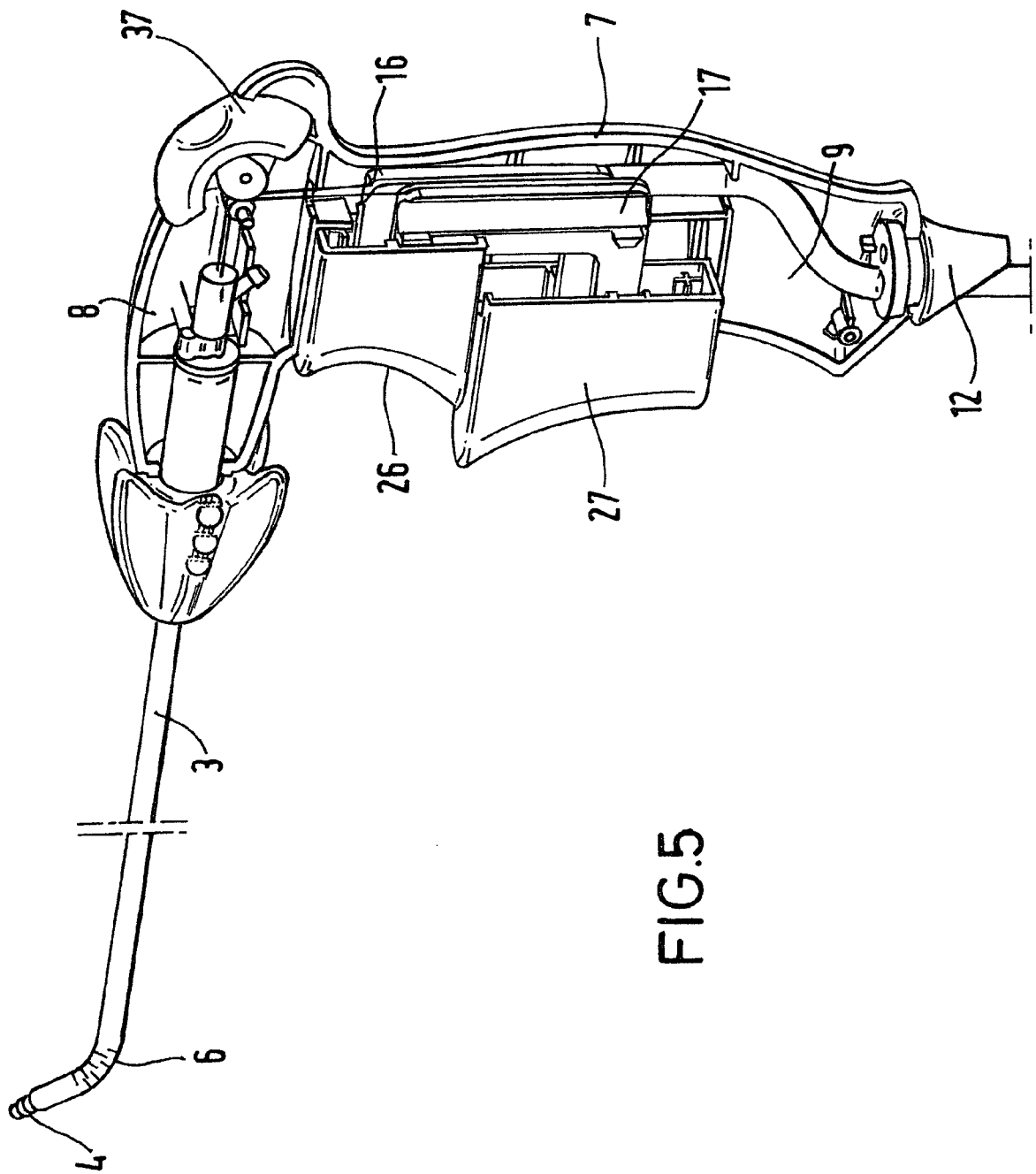
FIG. 5 is a perspective view, partly in section, of the instrument of FIG. 1 shown in its deflected position.

When the user depresses the button 26, the slider member 17 moves downwardly within the housing 7, pulling on the deflection cable 14 and causing the deflectable portion 6 to curve in one direction, as shown in FIG. 5. The slider member 16 moves upwardly to slacken the deflection cable 13, thereby allowing the deflection of the portion 6 to take place. The button 27 moves outwardly to compensate for the movement of the button 26 and the slider members 16 and 17.

Conversely, when the button 27 is depressed, the slider member 16 moves downwardly pulling on the deflection cable 13 and causing the deflectable portion 6 to curve in the opposite direction. The slider member 17 moves upwardly to slacken the deflection cable 14 to allow for the deflection to take place in the opposite direction. In either situation, if the user wishes to lock the deflectable portion 6 in a desired position, a locking mechanism 36 can be operated. The locking mechanism 36 comprises a member 37, rotatable about a pivot point 38. The member 37 is rotatable between a first position in which it is clear of the deflection cables 13 and 14, and a second locking position in which it contacts the cables 13 and 14 to lock them against the pulley 15. In this way, the surgical instrument 1 can be locked in position with a desired deflection being maintained until the locking mechanism 36 is released.

Figure 6:
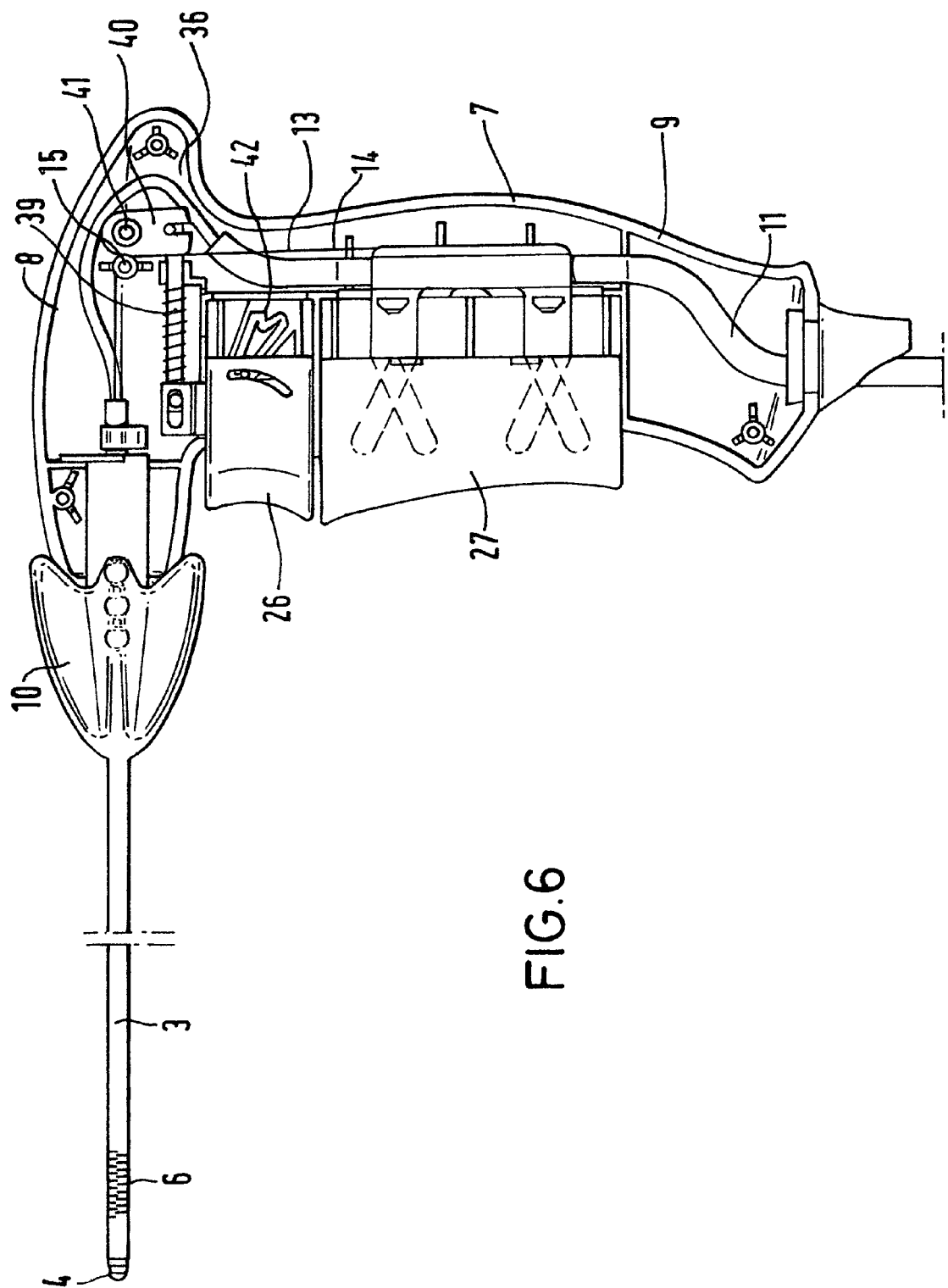
FIG. 6 is a perspective view, partly in section, of an alternative embodiment of surgical instrument in accordance with the invention.

FIG. 6 shows an alternative embodiment in which only one-way articulation is required. In this arrangement, similar features are designated with like reference numerals, and the button 27 operates entirely as previously described to move the slider member 16 downwardly and the slider member 17 upwardly to deflect the end effector 4. However, the button 26 is not used to cause an opposite deflection of the end effector 4, but instead operates the locking mechanism 36. When the button 26 is depressed, movement of that button is transferred to a slider bar 39, which causes rotation of an eccentric member 40. The eccentric member 40 rotates about a pivot 41 from a position in which it is clear of the deflection cables 13 and 14, to one in which it locks them against the pulley 15. The button 26 is mounted on an actuating mechanism 42, such that, when the button is depressed a first time, the locking mechanism 36 is applied; and, when that button is depressed a second time, the locking mechanism is released.

It will be appreciated that the arrangement of FIG. 6 only deflects the end effector 4 in a single direction, and that the swivel mechanism 10 is used to re-orient the shaft 3 so as to obtain deflection in other orientations. It will also be appreciated that a further simplification is to provide only a single button and a single slider member, and consequently only one deflection cable. In this circumstance, some other arrangement, such as a spring mechanism (not shown), will need to be provided for returning the deflectable portion 6 to its undeflected position when the button is released. As the second deflection cable performs this function in the illustrated embodiments, this will need to be effected by other means such as a spring arrangement.

However many deflection cables are employed, the linear movement of the one or more buttons 26 and 27, and the corresponding linear movement of the one or more slider members 16 and 17 means that the deflection of the deflectable portion 6 can be accurately controlled by the user of the instrument. Where two buttons 26 and 27 are employed, together with two slider members 16 and 17, deflection in two directions can be carefully effected.

Those skilled in the art will readily appreciate that other variants can be employed without departing from the scope of the present invention. For example, other locking mechanisms can be envisaged, acting not on the deflection wires but on the buttons 26 and 27 or slider members 16 and 17 themselves. One arrangement has a locking tab movable into a position in which it jams the movement of the buttons 26 and 27 or the slider members 16 and 17, thereby locking the tip of the instrument in position. Whichever type of locking mechanism is employed, the linear movement of the slider members 16 and 17 provides accurate control over the deflection of the deflectable portion 6 of the instrument.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. An articulated surgical instrument comprising:
   a handle;
   an actuating assembly associated with the handle;
   a shaft including a proximal end, a deflectable portion and an end effector, the proximal end of the shaft being coupled to the handle; and
   one or more deflection wires, each deflection wire having a proximal portion and a distal portion, each deflection wire's distal portion being connected to the shaft, and each deflection wire's proximal portion being connected to the actuating assembly,
   each movement of the actuating assembly causing each deflection wire to move to thereby cause a deflection of the deflectable portion,
   the actuating assembly comprising one or more actuators and one or more associated slider members, each slider member being movable linearly between a first position and a second position,
   the proximal portion of each deflection wire being connected to an associated one of the one or more slider members,
   a first one of each actuator and associated slider member having a cam track and the other having a cam follower, such that movement of the actuator by a user of the instrument causes a linear movement of the associated slider member from its first position to its second position so as to move at least one of the deflection wires, thereby causing a corresponding deflection of the deflectable portion
   each actuator comprising a button movable linearly between a first position and a second position to move the button's associated actuator and thereby the actuator's associated slider member, the linear movement of each actuator button being in a direction orthogonal to the linear movement of the actuator's associated slider member and causing the actuator's associated slider member to move between the slider member's first and second positions.

2. A surgical instrument according claim 1, wherein there is provided at least first and second deflection wires and respective first and second slider members.

3. A surgical instrument according to claim 2, wherein the first deflection wire is connected to the first slider member, and the second deflection wire is connected to the second slider member.

4. A surgical instrument according to claim 3, wherein the first and second slider members are each constituted by respective halves of a single slider assembly, each half being linearly movable with respect to the other.

5. A surgical instrument according to claim 3, wherein a first actuator constitutes said at least one actuator, the first actuator being provided with first and second cam tracks, and the first and second slider members each have a cam follower, the cam follower of the first slider member being received in the first cam track, and the cam follower of the second slider member being received in the second cam track.

6. A surgical instrument according to claim 5, wherein the first and second cam tracks are oriented in different directions, such that the movement of the first actuator causes the first slider member to move in a first direction and the second slider member to move in a different direction.

7. A surgical instrument according to claim 6, wherein the movement of the first actuator causes the second slider member to move in an opposite direction to that of the first slider member.

8. A surgical instrument according to claim 5, further comprising a second actuator for actuating a locking mechanism adapted to lock the deflection wires in position.

9. A surgical instrument according to claim 3, wherein there is provided first and second actuators.

10. A surgical instrument according to claim 9, wherein the first and second actuators are each provided with first and second cam tracks, and the first and second slider members each have two cam followers, the cam followers of the first slider member being received in the first and second cam tracks of the first actuator, and the cam followers of the second slider member being received in the first and second cam tracks of the second actuator.

11. A surgical instrument according to claim 10, wherein the first and second cam tracks of each actuator are oriented in different directions, such that the movement of the first actuator causes the first slider member to move in a first direction and the second slider member to move in the opposite direction, and the movement of the second actuator causes the second slider member to move in the first direction and the first slider member to move in the opposite direction.

12. A surgical instrument according to claim 11, wherein the movement of the first actuator causes a corresponding opposite movement of the second actuator, and the movement of the second actuator causes a corresponding opposite movement of the first actuator.

13. A surgical instrument according to claim 1, wherein the end effector is a pair of jaws.

14. A surgical instrument according to claim 1, wherein the end effector includes an electrosurgical electrode.

15. A surgical instrument according to claim 14, wherein the end effector is a bipolar electrode assembly.

* * * * *